(12) United States Patent
Sapp et al.

(10) Patent No.: US 8,148,142 B2
(45) Date of Patent: Apr. 3, 2012

(54) SYSTEM AND METHODS FOR PRODUCTION OF GASEOUS PRODUCTS FROM ORGANIC WASTE

(76) Inventors: Michael R. Sapp, Akron, OH (US); Rudy J. Wojtecki, Mantua, OH (US)

(*) Notice: Subject to any disclaimer, the term of this patent is extended or adjusted under 35 U.S.C. 154(b) by 1193 days.

(21) Appl. No.: 11/861,714

(22) Filed: Sep. 26, 2007

(65) Prior Publication Data

US 2008/0075638 A1     Mar. 27, 2008

Related U.S. Application Data

(60) Provisional application No. 60/827,148, filed on Sep. 27, 2006.

(51) Int. Cl.
*C12M 1/00* (2006.01)
*C12M 3/00* (2006.01)

(52) U.S. Cl. .................. 435/289.1; 435/399; 435/299.1; 435/300.1

(58) Field of Classification Search ............... 435/289.1, 435/299.1, 300.1; 422/168; 585/240; 210/603, 210/615, 150
See application file for complete search history.

(56) References Cited

U.S. PATENT DOCUMENTS 3,395,800 A * 8/1968 Kraus et al. ................... 210/768
6,254,775 B1   7/2001 McElvaney
6,905,601 B2 * 6/2005 De Baere et al. ............. 210/603
2004/0050777 A1 * 3/2004 Khan ............................. 210/603
2005/0126997 A1 * 6/2005 Langhans et al. ............. 210/629
2005/0167359 A1 * 8/2005 Wilkie .......................... 210/603
2006/0281161 A1 * 12/2006 Felder et al. .................. 435/168

FOREIGN PATENT DOCUMENTS

JP            02035995        *   2/1990

OTHER PUBLICATIONS

Ito, jp02035995 Derwent Abstract, Feb. 1990.*

* cited by examiner

*Primary Examiner* — Michael Marcheschi
*Assistant Examiner* — Shanta G Doe

(57) ABSTRACT

A system and methods for processing organic waste material for residential type environments includes a reactor tank dimensioned to receive a predetermined amount of organic material therein. The amount of organic material is selected based upon the size of the residential service area the system is servicing. The system includes homogenizing the volume of organic waste materials and selectively introducing the homogenized organic material into a reaction tank. A system for selectively removing gaseous by-products from the anaerobic digestion of organic material within the reactor tank is provided, along with a system for selective removal of waste solids from the reactor tank to provide for substantially continuous processing of materials and production of usable gases.

16 Claims, 3 Drawing Sheets

SYSTEM AND METHODS FOR PRODUCTION OF GASEOUS PRODUCTS FROM ORGANIC WASTE

The invention is directed to a system and methods for the manufacture of usable gas by anaerobic digestion of organic material in a residential type environment or for other applications handling organic waste products, wherein organic waste is supplied to an anaerobic bioreactor system for bioconversion of organic waste materials into useful gaseous and other byproducts by microbial digestion processes.

BACKGROUND OF THE INVENTION

Although a great amount of organic waste is produced in typical residential households and the like, there is no system available to allow for bioconversion of such wastes to produce usable gaseous byproducts for use in operating the residence. The systems for use in anaerobically digesting municipal sewage or livestock waste are not sufficient for the handling of residential wastes in a safe and convenient manner. Further, the municipal or commercial applications where organic waste materials are handled may be more effectively dealt with to produce useful energy.

In known anaerobic digestion systems, digestion rates can be reduced due to the lack of complete digestion. This can be due to poor growth of the microbes which digest the organic material as well as the lack of intimate contact with the microbes. It would be desirable to provide a system and methods which could be applied to residential organic waste materials to provide efficient and substantially automatic operation to enhance the growth of microbes and digestion of the waste materials.

It should be evident also that such prior systems are not designed for use in the residential environment, where concerns of safety, convenience, and effectiveness for wastes produced in such an environment are not considered, nor the possible nuisance that such systems may create due to odors or contamination. It would be desirable to provide systems and methods useful for such an environment, to provide cogeneration of energy resources for operation of residential systems. Problems in such an environment include reduced efficiency due to lack of providing an anaerobic environment in which bioconversion can be performed. Additionally, due to the nature of wastes in such an environment, systems are easily clogged from scum and inert materials within the waste stream, causing the need to unclog the system which can result in introduction of oxygen into the system. Other problems relate to the types of organic wastes produced in such an environment, where the content of a waste stream is non-uniform, and may vary in organic content significantly. It would be desirable to provide systems and methods for use in such environments which overcomes these problems.

SUMMARY OF THE INVENTION

The present invention comprises a system and methods for processing organic waste material comprising a feed system for selectively feeding waste organic material into the system for processing. There is further provided a system for homogenizing waste material from the feed system into an effluent stream. The effluent stream is selectively introduced into a reaction vessel or tank as a homogenized feed material, with the reaction tank having a predetermined volume for accumulating homogenized waste material. A plurality of substrates coated with a microbial growth medium are positioned within the reaction tank to facilitate the growth of predetermined microbes which react with the organic waste material to generate usable gas. A system for selectively removing generated gas from the reaction tank is provided along with a gas handling system for the removed gas. A waste removal system selectively removes spent waste material from the reaction tank subsequent to reaction with the microbes within the reaction tank. A control system provides selective control of the feed system, the system for homogenizing waste material, the system for removal of gas and the waste removal system to provide a supply of homogenized waste material to the reaction tank to maintain a predetermined amount of organic waste material in the reaction tank for reaction with microbes therein, and selectively removing spent waste material and generated gas from the reaction tank.

In the system, introduced organic material is anaerobically digested. Organic waste material may be accumulated in a holding tank, then combined with water or another fluid and processed to the desired particle size prior to periodic introduction into the reaction tank. In an embodiment, the waste materials are mixed in the holding tank to provide uniform organic content to the waste stream introduced to the reaction tank. The reaction tank is provided with an environment of predetermined microbes for processing of the organic material to produce gas, such as methane, and is shaped to promote digestion of the organic material, while providing a system for the capture and simple removal of gases generated by the digestion of the organic material. In an embodiment, the reaction tank is formed in a diamond-shape with a relatively smaller top and bottom portion and relatively larger middle section. Such a tank may be positioned in the ground in this orientation adjacent a residential or like facility, with the sides of the reaction tank formed to urge generated gases to the top portion of the system for selective removal. Similarly, digested organic material and inorganic materials in the tank are urged downwardly in the tank due to gravity, thereby more effectively separating such materials. A scum or sludge removal system may be provided in association with the uppermost portion of the tank, for periodically removing scum from the surface of the organic material slurry within the reaction tank. Similarly, a system may be provided at the bottom of the reaction tank for periodic removal of spent or inert solids. To enhance microbial growth in the reaction tank, both planktonic and free-floating aggregation of microbes, as well as colonization on a plurality of substrates upon which microorganisms are grown. In an embodiment, the substrates are formed with a fibrous growth medium forming a three dimensional matrix through which the organic slurry in the tank may flow to promote microorganism growth. The fibrous medium may be provided with a growth promoting substance to further enhance production of microbes for digestion of the organic material. The reaction tank may have access ports to position the plurality of substrates vertically within the open volume of the tank, and to facilitate removal and replacement of the substrates without disruption of the anaerobic environment within the tank. A control system operates these various systems to create a uniform stream of organic material content and to selectively introduce the content into the reaction tank at a predetermined particle size to facilitate interaction with the planktonic microbes and colonized microbes on the plurality of substrates. Gas production is enhanced by the selective removal of scum which tends to inhibit microbial action in the system, and the regular introduction of fresh organic material with selective removal of spent or inert materials. The digestion of the organic material in the reaction tank will produce methane gas and other gaseous by-products, and a valving system coupled to the reaction tank permits the selective removal of gaseous products from the reaction tank for use in residential, municipal, or commercial applications. The system and methods contemplate a modular approach to handling the amount of organic material for a given environment, wherein a plurality of units may be interconnected to effectively handle the organic material.

Other features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DESCRIPTION OF EMBODIMENTS OF THE INVENTION

Figure 1:
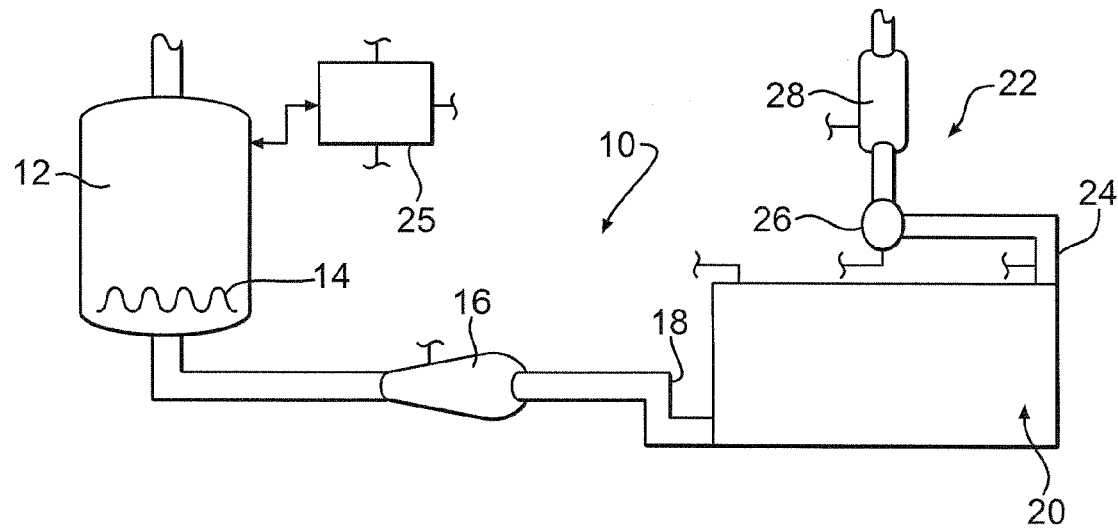
FIG. 1 is a schematic diagram of an organic waste processing system according to an embodiment of the present invention.

Referring to FIG. 1, an embodiment of the system 10 for processing residential organic waste material comprises a holding tank 12, into which organic and inorganic waste materials are selectively introduced by a user. In the environment of residential or like facilities, the types of waste, from generated or naturally occurring organic wastes, vary significantly, and the organic content of the waste stream also varies accordingly. According to an embodiment, the waste stream and organic content thereof is made more uniform by selecting the size of the holding tank 12 in association with the size of the household(s) or facilities to be serviced by the system 10. As the waste stream from such facilities tends to be substantially uniform for a given volume of waste, the size of holding tank 12 is chosen to accommodate at least the minimum volume of waste from a given service area to according to this determination. In general, the holding tank 12 may have a volume equal to approximately at least one weeks worth of waste produced from the service area. In this way, the organic content of the waste stream is substantially uniform over the predetermined volume of waste. It is also possible to provide a modular system where a holding tank 12 may serve multiple facilities, or a number of smaller tanks 12 are provided to work in tandem for supplying an amount of organic material to be processed. To further provide for uniformity of waste stream organic content, the waste material introduced into the holding tank 12 is mixed, either intermittently or selectively prior to introduction for processing. A mixing system 14 is provided within the holding tank 12, which may be of any suitable type, such as an auger arrangement within the bottom portion of the tank 12. Such a system may also allow for size reduction of waste materials within the holding tank 12 to facilitate break down of the organic material. Other mixing or blending systems are also contemplated. Alternatively or in addition, chemical additives may be used to facilitate initial breakdown of various organic materials to be processed in the system 10.

It should also be recognized that for convenience, any type of waste material may be introduced into the system 10, including inorganic and inert materials, to facilitate convenient use of the system 10. This allows all waste materials produced in the residential type service area to be introduced into the system, with inorganic and inert materials being processed through the system as will be hereinafter described, and removed subsequent to processing for post-processing procedures. Such materials may be ground into a powder form subsequent to removal from the system 10, or otherwise processed to form additional usable materials. As the conversion or organic material is not completely efficient, the processed solids are selectively and intermittently removed from the system 10 and may be further processed into other output products. For example, such materials may be usable as a semi-organic soil treatment, high quality fertilizer, plant food or other commercial products. Alternatively, such materials may be used as fillers in other manufacturing processes, as the material may be substantially inert and non-reactive with other chemical elements.

In this embodiment, the system 10 is designed to work effectively in an automatic manner, allowing a user to simply dispose of waste materials into the holding tank 12, with subsequent processing being performed automatically. In the system, the mixed and possibly size-reduced waste material is selectively and intermittently fed to a system 16 for homogenizing the waste stream into a substantially uniform slurry, which is in turn introduced into a reaction tank 20 for processing. The system 16 for homogenizing the waste material may be of any suitable type, such as a grinder pump to which the waste material and water or another fluid is pumped. A backflow prevention valve 18 may be provided to prevent possible backflow of material from the reaction tank 20. The valve 18 also facilitates maintaining an anaerobic atmosphere within the reaction tank 20, by sealing the conduit through which the waste material is introduced to the tank 20, until additional material is to be added to the tank 20, at which time the pumping of material into the tank is performed without introducing oxygen into the system. In the homogenizing system 16, it is desirable to comminute the waste material to form solids having an average particle size preferably between 0-500 µm. During grinding, the processed waste material is mixed with a suitable amount of water to achieve a slurry of a desired consistency, such as between 1 and 50 percent solids by weight. Slurries with the particles sizes in the above range interact in a specific manner with microbial constituents within the reaction tank.

The activated organic slurry produced in the homogenizing system 16 is pumped through a sealed conduit through valve 18 to the reaction tank 20. Similar to the holding tank 12, the reaction tank 20 is dimensioned to have a predetermined volume corresponding to the volume of the holding tank and designed for use by between 1 to 10 residential housing units for example. The approximate volume of organic material slurry to be produced according to the volume of waste materials, is selected and the volume of the tank 20 chosen such that the expected volume of slurry will fill the volume of the reaction tank 20 to a desired level that can be substantially maintained. The sizes of holding tank 12 and reaction tank 20 may also be scaled up in size as necessary for use in other applications. Also, a plurality of reaction tanks 20 may be connected to provide the desired processing volume for a given application, making the system very flexible to accommodate a specific situation. If a plurality of reaction tanks 20 are connected, effluent from one system may be selectively directed to a desired reaction tank 20 regardless of the particular facility from which it is generated, or to accommodate fluctuations in effluent volume. In this manner, the system can be tailored to a given application without significant changes to the basic module comprising the system of FIG. 1.

As will be hereinafter described in more detail, the organic material introduced into the reaction tank 20 is effectively digested by microbial action to produce methane and other gaseous components. The gas produced by these microbes may contain a small quantity of sulfur dioxide, which is corrosive, and it may therefore also be desirable to provide a sulfur dioxide trap to remove this gas or other unwanted components from the gaseous products supplied from the system 10. For example, by bubbling the raw biogas through distilled water, the sulfur dioxide will dissolve readily in the water and be removed from the gaseous products. Other suitable systems for removing unwanted constituents are contemplated. The methane gas product produced may be a medium-BTU gas, which can be used in a variety of applications. For example, the methane may be used to run an electric generator to produce power for running electrical systems in the residential or other service area, or for sold for use in the general power grid in the area. Alternatively, the gas product may be processed to be used for similar applications as propane or natural gas in cooking, heating, refrigeration and/or lighting. It is even possible with further processing to convert the gas products into liquid fuel, such as gasoline or diesel if desired. In this way, the gas produced may be used as a transportation fuel source, for operating a vehicle or the like. In using a plurality of modular systems connected together, the amount of gas products may allow production of sufficient amounts of fuel to run a car for extended periods, or for a municipal or commercial environment, enough gas to run buses, fire and rescue and police vehicles for example.

The generated gaseous products are selectively removed from the reaction tank 20 by a gas handling system 22, which may comprise a pressure-activated valve 24, a gas compressor 26 and a gas storage tank 28 for example. The valve 24 may be activated to release gas from the reaction tank 20 when a predetermined pressure is reached within the tank 20. This predetermined pressure will generally be chosen to reflect that pressure within the tank 20 where a suppressing effect on digestion begins to occur. As the pressure within the tank 20 rises as organic material is digested, the digestion by the microbes can be adversely impacted, as the microbes are not operating within their normal conditions. It may also be possible to provide for release of gas to meet on-demand needs within the residential service area. The valve 24 again preserves the anaerobic atmosphere within the tank 20 as desired. Further, the gas compressor 26 may be explosion proof to enhance safety of the system. Any other suitable alternative handling of the gaseous components is contemplated in the invention. As the system 10 is modular, it is also contemplated that a plurality of systems 10 are connected, and the gas handling system 22 designed for handling the gaseous products produced from the multiple systems, which may be connected to a single output stream which for effective handling and distribution.

The activated organic slurry produced in the homogenizing system 16 is pumped through a conduit and valve 18 to the reaction tank 20. The reaction tank 20 is dimensioned for use by between 1 to 10 residential housing units, which produce approximately the predetermined amount of organic material required to fill the capacity of the reaction tank. The reaction tank 20 may also be scaled up in size as necessary for use in municipal or commercial applications. The modular system then allows a plurality of systems 10 to be connected to handle the desired application, and could be scaled up in this way for use in municipal or commercial applications.

Figure 2:
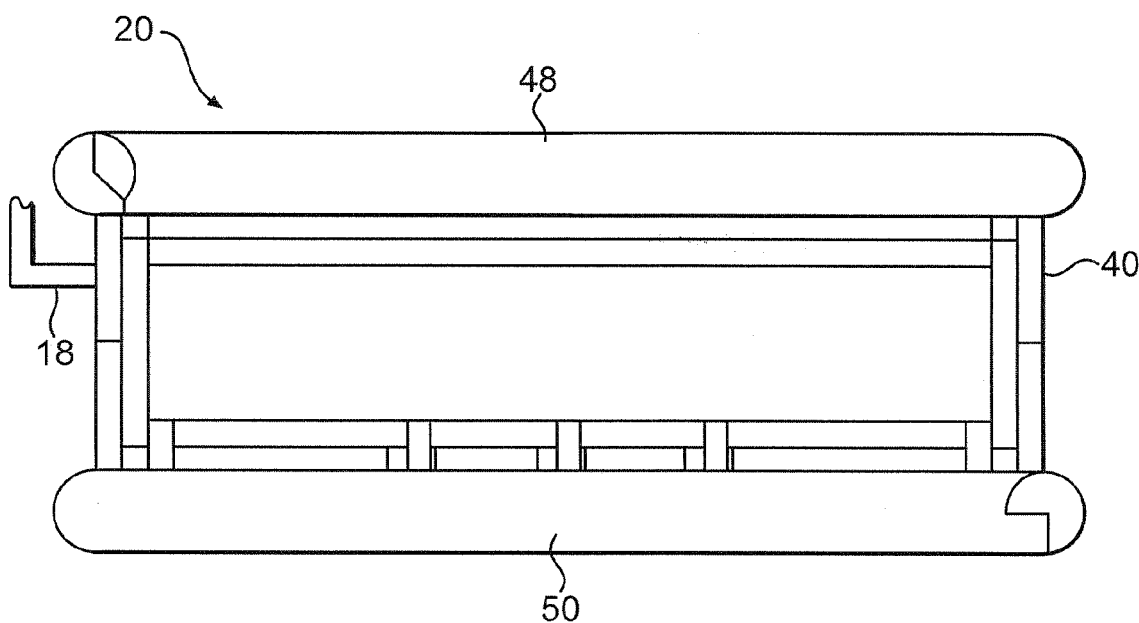
FIG. 2 is a partial schematic diagram of the reaction tank shown in the embodiment of FIG. 1.
Figure 3:
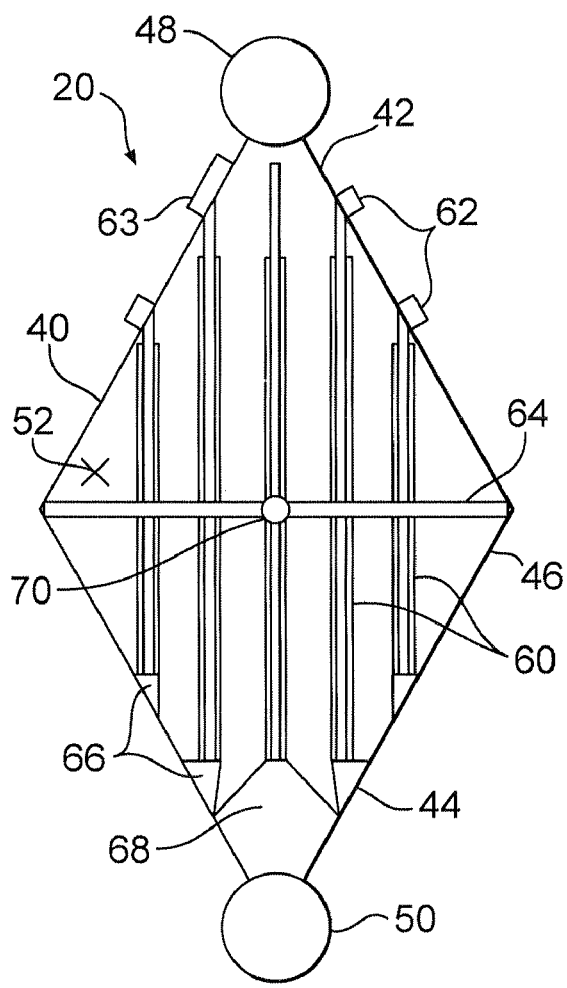
FIG. 3 is a schematic cross-sectional view of the reaction tank shown in FIG. 2.

Referring now to FIGS. 2 and 3, the reaction tank 20 in this embodiment is formed of a housing 40 shaped in a diamond-type shape. The housing 40 has relatively small upper and lower portions 42 and 44, and a relatively larger middle section 46. Such a tank 20 may be positioned in the ground in this orientation adjacent a residential service area or the like, such that the waste material feed systems and other systems can be coupled directly from and to the service area. Alternatively, the housing 40 may be positioned in other than the vertical orientation if desired, with other systems moved to accommodate the horizontal or another angular orientation. The system 10 is thus effectively invisible to the surrounding environment, with access for maintenance activities provided by a small access at the top portion of the tank 20. The other sub-systems are easily positioned in the residential facilities in a typical fashion. The sides of the housing 40 are formed to urge generated gases to the top portion of the system 10 for selective removal via the gas handling system 22. Similarly, digested organic material and inorganic materials in the housing 40 are urged downwardly in the tank due to gravity, thereby more effectively separating such materials. In digestion of organic materials, there may be produced a scum type of material that floats to the top of the slurry. The formation of scum on the top surface of the slurry can act to inhibit digestion of the organic material in this top region of the reaction tank, and removal of any generated scum is desired. A scum or sludge removal system 48 may be provided in association with the uppermost portion of the housing 40, for periodically removing scum from the surface of the organic material slurry within the reaction tank. The height of the slurry in the housing 40 is maintained to allow the scum removal system 48 to be effective to remove scum from the surface thereof. In an embodiment, the scum removal system may be an auger transport system coupled to the housing volume at the uppermost portion of the housing 40. The scum removal system 48 may be operated intermittently via a control system, or formation of scum may be monitored to selectively remove scum when generated.

Similarly, desired digestion rates may be reduced if the volume of inorganic waste exceeds a predetermined volume within the housing 40. A waste removal system 50 may be provided at the bottom of the housing 40 for periodic removal of spent or inert solids. The waste removal system 50 may be of any suitable type, and may be similar to the auger transport system as described with reference to the scum removal system 48 above. The control of the waste removal system 50 may be at predetermined intervals to maintain a desired mix of organic material in the slurry within the housing 40 for digestion and production of gas, or the volume may be monitored and system 50 automatically operated as needed. The shape of housing 40 facilitates removal of solids from the system, and such solids are funneled to the waste removal system 50 at the bottom portion of the housing 40. To further facilitate movement of solid wastes to the removal system 50, a plurality of substrates 60 to be described hereafter, are spaced within the housing 40 and provide intermittent baffles that tend to suspend the solids so that they fall to the bottom of the housing 40. The slurry within the housing 40 is selectively circulated by a circulation system 52 to maintain proper digestion of organic materials while promoting this action in facilitating removal of spent solids and movement of scum to the scum removal system 48. As previously described, the system is modular to allow a plurality of reaction tanks 20 to be connected, and similarly, the scum removal system 48 and waste removal system 50, may be connected to a single output stream which for effectively handling these materials.

To enhance microbial growth in the reaction tank, both planktonic and free-floating aggregation of microbes, as well as colonization on a plurality of substrates 60 upon which microorganisms are grown are utilized. In an embodiment, a plurality of substrates 60 are positioned in spaced apart relationship within the volume of the housing 40. The substrates 60 are formed with a fibrous growth medium forming a three dimensional matrix through which the organic slurry in the tank may flow at a reduced rate to promote microorganism growth and digestion. The plurality of substrates 60 may include a plurality of small and large substrates, matching the vertical height of housing 40 at different locations within its volume as shown in FIG. 3. Each of the substrates 60 is selectively positioned within the housing 40 through a respective access opening 62 formed in the top portion of the housing 40. A plurality of access openings 62 are provided in the proper position to introduce the substrate 60 into the interior volume in a substantially vertical position, with this position being maintained in association with a center support system 64 positioned on the interior volume of the housing 40. The center support 64 may facilitate forming a sturdy structure in association with the sides of the housing 40 and in positioning the substrates 60 in association with platforms 66 formed on the bottom interior sides of housing 40. A center platform 68 is designed for positioning the center substrate 60. As can be seen in FIG. 3, the center substrate 60 is not in contact with the top of the housing 60, and is positioned in spaced relation to any access port 62. To facilitate positioning of the center substrate 60, a positioning member 70, such as a small cylinder or the like, is provided lengthwise in the housing 40, the forms a pivot about which the substrate 60 can be properly positioned in association with the center platform 68. Additionally, a larger access port 63 is provided adjacent the center location to allow for insertion and removal of the center substrate 60. A handle (not shown) may extend to facilitate insertion and/or removal of the center substrate 60. In this manner, each of the substrates 60 is easily positioned in the desired location through one of the access ports 62, which are then closed and sealed to enable the anaerobic environment to be maintained. In this manner also, the substrates 60 are easily maintained or replaced as needed for effective operation in the system. If the housing 40 is positioned in a different orientation, the substrates 60 may be introduced through other portions of the housing 40 accordingly.

Figure 5:
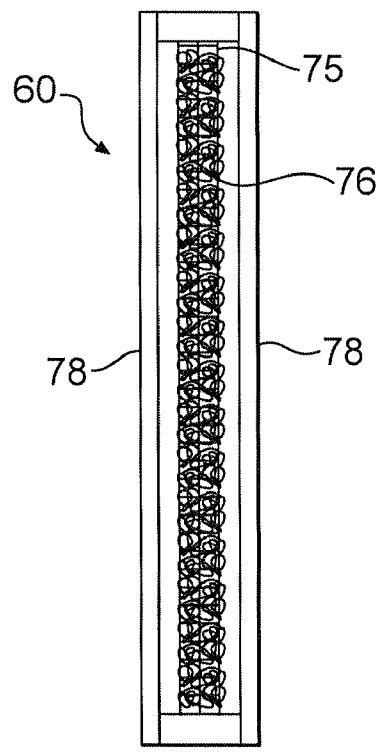
FIG. 5 is a schematic illustration of the positioning of a substrate within the reaction tank according to an embodiment.
Figure 4:
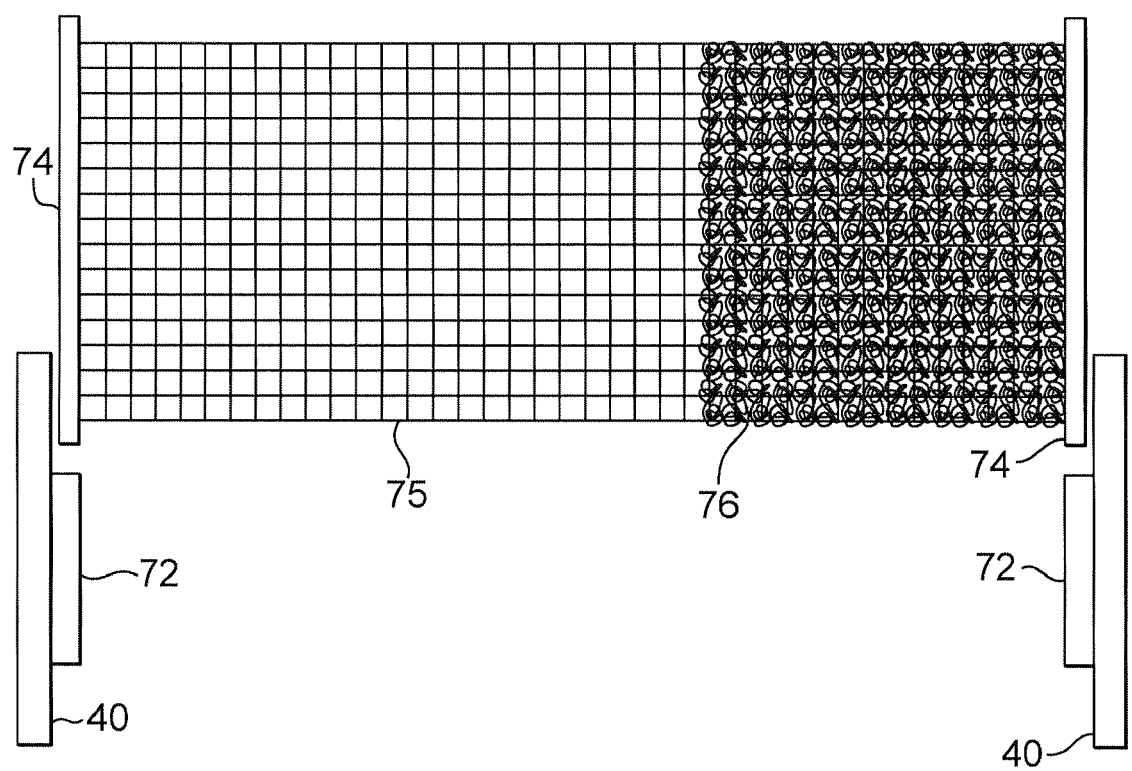
FIG. 4 is a schematic top view of a substrate according to an embodiment of the invention, showing a fibrous medium over a portion thereof.

As shown in FIGS. 4 and 5, to further facilitate positioning of the substrates 60 within the housing 40, supporting rails 72 may be provided on the interior volume of the housing 40. The rails 72 maintain the position of the substrates 60 without interfering with the growth of microorganisms or proper digestion of organic materials. The rails may mate with a frame support member 74 provided on each side of the substrate 60. A supporting mesh or screen 75 may be provided with a fibrous medium 76 to form the basic substrate 60, and provide a medium which has an extremely large surface area with a large amount of sites for microbial colonization. As seen in FIG. 5, the substrates 60 may also be provided with a gelatinous dissolvable microbial growth promoting film 78 adjacent the fibrous medium 76 to further enhance production of microbes for digestion of the organic material. A combination of cellular mitosis and bacterial recruitment provide increased microbial populations.

Turning back to FIG. 1, a control system 25 operates the various systems to create a uniform stream of organic material content and to selectively introduce the content into the reaction tank 20 at a predetermined particle size to facilitate interaction with the planktonic microbes and colonized microbes on the plurality of substrates 60. Gas production is enhanced by the selective removal of scum by system 48 which tends to inhibit microbial action in the system. This along with the regular introduction of fresh organic material from the homogenization system 16, and the selective removal of spent or inert materials via system 50, provide for the digestion of the organic material with increased efficiency. The system 10 and methods according to the invention will produce methane gas and other usable gaseous and solid by-products. A valving system 24 coupled to the reaction tank 20 selectively permits the removal of gaseous products from the reaction tank 20 for use in a residential service area. It may also be possible to provide systems and methods according to the invention that would facilitate co-generation of fuel or power requirement in municipal or commercial applications.

The shape of the reaction tank 20 facilitates removal of spent organic solids which have settled within the reaction tank 20 after anaerobic digestion. The system 50 for selective removal of solids from the reaction tank 20 allows for automatic renewal of organic materials within the system, and evacuates such materials for subsequent processing away from the site of the system 10. Periodic removal of solids waste may be preformed similar to typical trash removal from the residential service area. Alternatively, the system 50 may transport the materials to a leech field or other suitable disposal location. As the predetermined volume of spent waste is removed from the reaction tank 20, a corresponding volume of activated organic waste is pumped into the reaction tank 20 to maintain a substantially constant volume of slurry within the reaction tank 20. The use of both planktonic and colonized microbes in the system 10 provides for more efficient digestion of organic materials, and the plurality of substrates 60 may be initially dosed with anaerobic bacteria and then infiltrated with a gelatinous bacterial growth medium. The substrates 60 will also provide a medium on which microbe growth will proliferate when in the anaerobic environment created by the system. The system and methods of the invention provide distinct advantages in having an optimal combination of desired properties for use in residential environments. In combination with a plurality of the systems, other applications, such as municipal or commercial applications may be accommodated. The provision of a substantially homogenous organic material stream promotes the conversion of biodegradable organic material to gaseous and soluble products, while the system allows for retention of slowly metabolized solids for prolonged periods of time so as to be effectively digested.

The present disclosure includes that contained in the appended claims, as well as that of the foregoing description. Although the invention has been described with a certain degree of particularity in its preferred form, it should be understood that the present disclosure of the preferred form is made only as an example and that numerous changes to the elements of the system may be applied without departing from the spirit and scope of the invention.

What is claimed is:

1. A system for the manufacture of usable gas by anaerobic digestion of organic material comprising:
   a supply of organic material,
   a reaction tank having a predetermined volume for accumulating the organic material a plurality a substrates having predetermined microbes associated therewith which react with the organic material to generate usable gas, and wherein the plurality of substrates comprise an artificial, fibrous growth medium having a microbial growth promoting film allowing for the enhanced growth of microbes, a screen housing the fibrous growth medium, and the film being a gelatinous, dissolvable microbial growth promoting substance, a gas removal system for selectively removing generated gas from the reaction tank.

2. The system according to claim 1, further comprising a system for homogenizing organic material designed to comminute the solid organic material to a predetermined particle size range.

3. The system according to claim 2, wherein the system for homogenizing waste material produces waste material of a predetermined particle size of between substantially zero and 500 microns.

4. The system of claim 1, further comprising a waste removal system to selectively remove spent waste material from the reaction tank.

5. The system according to claim 1, wherein the reaction tank is formed to have a shape with relatively smaller top and bottom portions about a relatively larger middle portion, wherein gases produced in the system are urged to the top portion and spent waste solids in the system are urged to the bottom portion.

6. The system according to claim 1, further comprising a scum removal system provided in association with the top portion of said reaction tank to selectively remove scum from the top surface of the slurry within the reaction tank.

7. The system according to claim 6, wherein the scum removal system is a screw conveyance system extending into contact with the top of the material slurry within the reaction tank.

8. The system according to claim 4, wherein the waste removal system is provided in association with the bottom portion of said reaction tank to selectively remove waste solids from the bottom portion of said reaction tank.

9. The system according to claim 8, wherein the waste removal system is a screw conveyance system communicating with the interior volume of the reaction tank to receive waste solids accumulated by gravity at the bottom of the reaction tank.

10. The system according to claim 1, wherein the plurality of substrates are positioned in a substantially vertical orientation within the reaction tank allowing for the enhanced growth of anaerobic bacteria with the reduction of and protection from sediment populating and congesting the fibrous growth medium.

11. The system according to claim 10, wherein the plurality of substrates are selectively insertable and accessible via a plurality of access ports formed in the reaction tank.

12. The system according to claim 10, wherein the plurality of substrates are positioned on support platforms formed on the interior of the reaction tank allowing for the enhanced growth of anaerobic bacteria with the reduction of and protection from sediment over populating and congesting the fibrous growth medium.

13. The system according to claim 1, wherein the predetermined volume of the reaction tank is selected to be approximately the volume of organic material produced in approximately one week from a predetermined service area and the predetermined service area comprises one to ten facilities.

14. A system for the manufacture of usable gas by anaerobic digestion of organic material comprising:

a supply of organic material, a reaction tank having a predetermined volume for accumulating the organic material, a plurality a substrates having predetermined microbes associated therewith which react with the organic waste material to generate usable gas, wherein the substrates are spaced within said reaction tank on intermittent baffles that are configured to suspend solids so the solids fall to a bottom of said reaction tank, allowing for the enhanced growth of anaerobic bacteria with the reduction of and protection from sediment populating and congesting the growth medium;

a gas removal system for selectively removing generated gas from the reaction tank.

15. The system of claim 1, further comprising a feed system for feeding organic material to the reaction tank.

16. The system of claim 1, further comprising a system for homogenizing organic waste material into an organic material slurry, wherein the slurry is selectively introduced into a reaction tank as a homogenized feed material.

\* \* \* \* \*